(12) United States Patent
Simons-Nikolova et al.

(10) Patent No.: US 7,769,635 B2
(45) Date of Patent: Aug. 3, 2010

(54) WEIGHT MANAGEMENT SYSTEM WITH SIMPLE DATA INPUT

(75) Inventors: Mariana Simons-Nikolova, Eindhoven (NL); Maarten Peter Bodlaender, Eindhoven (NL); Annelies Goris, Eindhoven (NL); Olivier Schneider, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 103 days.

(21) Appl. No.: 12/066,675

(22) PCT Filed: Aug. 31, 2006

(86) PCT No.: PCT/IB2006/053039

§ 371 (c)(1),
(2), (4) Date: Mar. 13, 2008

(87) PCT Pub. No.: WO2007/031895

PCT Pub. Date: Mar. 22, 2007

(65) Prior Publication Data

US 2008/0255955 A1    Oct. 16, 2008

(30) Foreign Application Priority Data

Sep. 15, 2005    (EP) .................................. 05108465

(51) Int. Cl.
*G06Q 1/12*    (2006.01)
(52) U.S. Cl. .............................. 705/21; 705/14; 705/15; 235/462.46; 434/127; 707/1
(58) Field of Classification Search ................... 705/21, 705/14–15; 235/462.46; 434/127; 707/1
See application file for complete search history.

(56) References Cited

U.S. PATENT DOCUMENTS 4,891,756 A    1/1990    Williams, III (Continued)

FOREIGN PATENT DOCUMENTS

EP    1122524 A2    8/2001

(Continued)

OTHER PUBLICATIONS

J. Parkka et al., A Wireless Wellness Monitor for Personal Weight Management, Information Technology Applications in Biomedicine, Proceedings 2000 IEEE EMBS International Conference, pp. 83-88.

*Primary Examiner*—Vanel Frenel
(74) *Attorney, Agent, or Firm*—Yan Glickberg (57) ABSTRACT

A weight management system comprises a cash register (CRS), a user client (UC) and a weight management module (WM), coupled via a wide area network (WAN). A user has a personal card (PC) with a code, the code identifying the user to the cash register and being related to a user ID. The cash register system (CRS) is arranged for sending, when the user pays the food item, corresponding food intake information and the user ID to the weight management module (WM). The weight management module (WM) comprises a food information system, a calorie intake component and a calorie balance component. The food information system stores a respective calorie content for a plurality of food items. The calorie intake component is coupled to the food information system and calculates an amount of calories taken by the user based on the received food intake information.

19 Claims, 7 Drawing Sheets

U.S. PATENT DOCUMENTS

| | | | |
|---|---|---|---|
| 4,951,197 A * | 8/1990 | Mellinger | 600/300 |
| 5,704,350 A | 1/1998 | Williams, III | |
| 5,839,901 A * | 11/1998 | Karkanen | 434/127 |
| 6,040,531 A | 3/2000 | Miller-Kovach | |
| 6,083,006 A * | 7/2000 | Coffman | 434/127 |
| 2002/0027164 A1 * | 3/2002 | Mault et al. | 235/462.46 |
| 2004/0118618 A1 | 6/2004 | Davidson | |
| 2005/0021371 A1 | 1/2005 | Basone | |
| 2005/0071197 A1 | 3/2005 | Goldberg | |
| 2005/0113650 A1 | 5/2005 | Pacione | |

FOREIGN PATENT DOCUMENTS

| | | |
|---|---|---|
| JP | 2001101157 | 4/2001 |
| WO | WO0189365 A2 | 11/2001 |
| WO | WO03069427 A2 | 8/2003 |
| WO | WO2004107227 A1 | 12/2004 |

\* cited by examiner

WEIGHT MANAGEMENT SYSTEM WITH SIMPLE DATA INPUT

FIELD OF THE INVENTION

The invention relates to a weight management system, a personal card for use with the weight management system and an activity registration device for use with the weight management system.

BACKGROUND OF THE INVENTION

Overweight and obesity are growing problems, for example over 60% of the American population is classified as overweight or obese. Weight gain occurs when a human being has a higher energy consumption or intake (food) than energy expense (resting metabolic rate+activity). Since this disbalance causes the weight gain problem, many weight loss programs require that users log the food consumed, and activities done in order to estimate the calorie balance.

There exist tables and equations for converting nutrition values and activities into calorie intake and expenditure, respectively. However, calorie counting manually is a cumbersome process requiring knowledge, time, effort, recording and discipline. Thus, calorie logging is a problem for many people and hence it is a challenge for researchers to find a solution therefore.

This problem has been acknowledged before. It has been proposed to provide at least some computerized record keeping schemes to persons engaged in foodstuff selection and recording. Recently, U.S. Pat. Nos. 4,891,756 and 5,704,350 propose an alternative solution to the problem of caloric management. They disclose systems consisting of a computer and/or personal (mobile) user device, e.g. PDA, logging the type and quantities of food and beverages consumed. The logging process is based on a manual selection from a food database, presented to the user via GUI. Thus, the process is still time consuming and requires regular recording that becomes a pitfall for the user. The simpler the logging can be made, the higher the percentage of users who will adhere to it.

For example, the Weight Watchers have introduced in their weight control programs a diet POINT® system as a replacement of direct calorie counting. Further, a daily calorie balance is substitute with a recommended daily POINT® target. A POINT® (U.S. Pat. No. 6,040,531) is single-valued nutritional indicators calculated from the calorie, fat and fiber values in a known quantity of consumed food. A second publication of Weight Watchers (US20040118618) covers a mechanism for determining points of unknown quantities or combinations of foodstuffs such as in an evening meal. Recently, Weight Watchers introduced Weight Watchers On-the-Go™, a PDA-based software that aids the user in calculating and recording his/her points in a daily log. Then, the user can synchronize his/her log with the Weight Watchers-online website in order to get a personal feedback. Summing up, while less precise, the POINT® system simplifies the manual calorie intake counting by users.

Further, WO0189365 explores the applicability of POINT® to resting metabolic rate (RMR) and physical activity of a person in order to simplify their recording. As a result, resting and activity points have been introduced. An alternative to the Weight Watchers POINT® is proposed by EP 1122524 and WO200369427. These documents focus on audio recording and voice recognition in calorie logging instead of manual selection. The essential difference between the two documents is in the complexity of the personal user devices involved. EP 1122524 proposes that such a personal user device incorporates both—a voice recognition unit as well as a data processing unit for processing the information. Such a construction substantially increases the cost of the personal device making it less affordable to the mass user. That is why WO200369427 decouples these units allowing the data processing unit to be at remote location connected to the personal user device via Internet. This simplifies the personal user device and increases its affordability.

Each of the above mentioned systems require either manual or voice/picture recognition of user's input in logging the food consumed and activities done. This is time-consuming and especially in crowded public areas, like canteens, restaurants, and fitness centers, even inapplicable. Users often either do not have that opportunity or forget. Entry at a later moment is typically inaccurate due to the limited ability of users to exactly remember what they ate and did.

OBJECT OF THE INVENTION

It is an object of the invention to provide a more simple way of data input for a weight management system.

SUMMARY OF THE INVENTION

This object is achieved by providing a weight management system comprising:
  a cash register, a user client and a weight management module, coupled via a wide area network, and
  a personal card with a code, the code identifying a user to the cash register and being related to a user ID,
  the cash register being arranged for sending, when the user pays the food item, corresponding food intake information and the user ID to the weight management module,
  the weight management module, comprising:
    a food information system for storing a respective calorie content for a plurality of food items,
    a calorie intake component, coupled to the food information system, for calculating an amount of calories taken by the user based on the received food intake information,
    a calorie balance component, coupled to the calorie intake component, for calculating a calorie balance for the user, based on the amount of calories taken by the user.
  the user client being arranged for obtaining the calorie balance from the weight management module and comprising output means for providing the calorie balance to the user.

Large caterers tightly manage the quality and quantities of the food they sell. For example, a caterer or food retailer may know the nutritional values of their offerings within an error margin of 5%. There exist systems (for example in Marketing companies) that scan product barcodes of purchased food, and upload that information to a central system. These are not (yet) used for weight management, and typically do not work in a restaurant/canteen/food chain setting. This invention takes advantages of the large and accurate information databases of food suppliers. This invention also takes advantage of the records most businesses keep about the goods they sell to their customers. The invention further takes advantage of the fact that a lot of purchases involve the use of a personal card and the fact that more and more functions are integrated in one personal card.

In a preferred embodiment the weight management system further comprises:
- a further personal card with a further code, the further code identifying a user to an activity registration device and being related to the user ID,
- the activity registration device being coupled to the weight management module via the wide area network and being arranged for registering the performance and sending, when the user performs an activity, corresponding activity information and the user ID to the weight management module, the weight management module further comprising:
- an activity information system for storing a respective calorie expense for a plurality of activities,
- a calorie expenditure component, coupled to the activity information system, for calculating an amount of calories expended by the user based on the received activity information, and wherein
- the calorie balance component is further coupled to the calorie expenditure component and is arranged for calculating the calorie balance further based on the amount of calories expended by the user.

This embodiment takes advantage of the fact that the fitness centers have precise information on physical parameters related to the range of activities they offer. The further personal card may be the same card as the personal card with the code for identifying the user to the cash register. The activity registration device may register the activity itself. For example, a number of kilometers rode on a bike may be measured. The user's activities may alternatively be registered, using a member registration card, which the user needs for entering specific areas where specific activities are performed. For example, the system may register 30 minutes of presence at a squash court. By comparing food intake to calorie expenditure, a prediction may be made whether the user will gain or lose weight. The calorie balance may indicate when a user should alter eating or activity patterns for obtaining a preferred weight.

In an embodiment of the weight management system according to the invention the user client comprises input means for enabling the user to provide food intake information and activity information for sending to the weight management module. Probably, not all activities of the user are registered by activity registration devices and not all consumed food is bought at businesses, participating in the weight management system. This embodiment allows a user to complete the data input for the weight management system.

In an embodiment according to the invention the food intake information and/or the activity information is formatted according to a uniform weight management system format. This makes it easy for the weight management module to calculate the calorie balance in a situation where food may be bought at several locations with in itself different ranges of food.

In an alternative embodiment the calorie intake component comprises a converter for converting the food intake information to a weight management system format. This embodiment has the advantage that a large variety of cash registers and activity registration devices may be used with the system, without requiring large adaptations to those systems.

In a further embodiment the food information system comprises a calorie content for a plurality of food ingredients and the weight management system further comprises a calorie source group client, coupled to the food information system for calculating the food intake information for a new food item, based on a list of ingredients of the new food item. This embodiment makes it possible for a food supplier to sell new products or menus, which are not yet known by the weight management system. When a user buys these new products or menus, the corresponding food intake information is available for sending to the weight management module.

These and other aspects of the invention are apparent from and will be elucidated with reference to the embodiments described hereinafter.

DETAILED DESCRIPTION OF THE INVENTION

Figure 1:
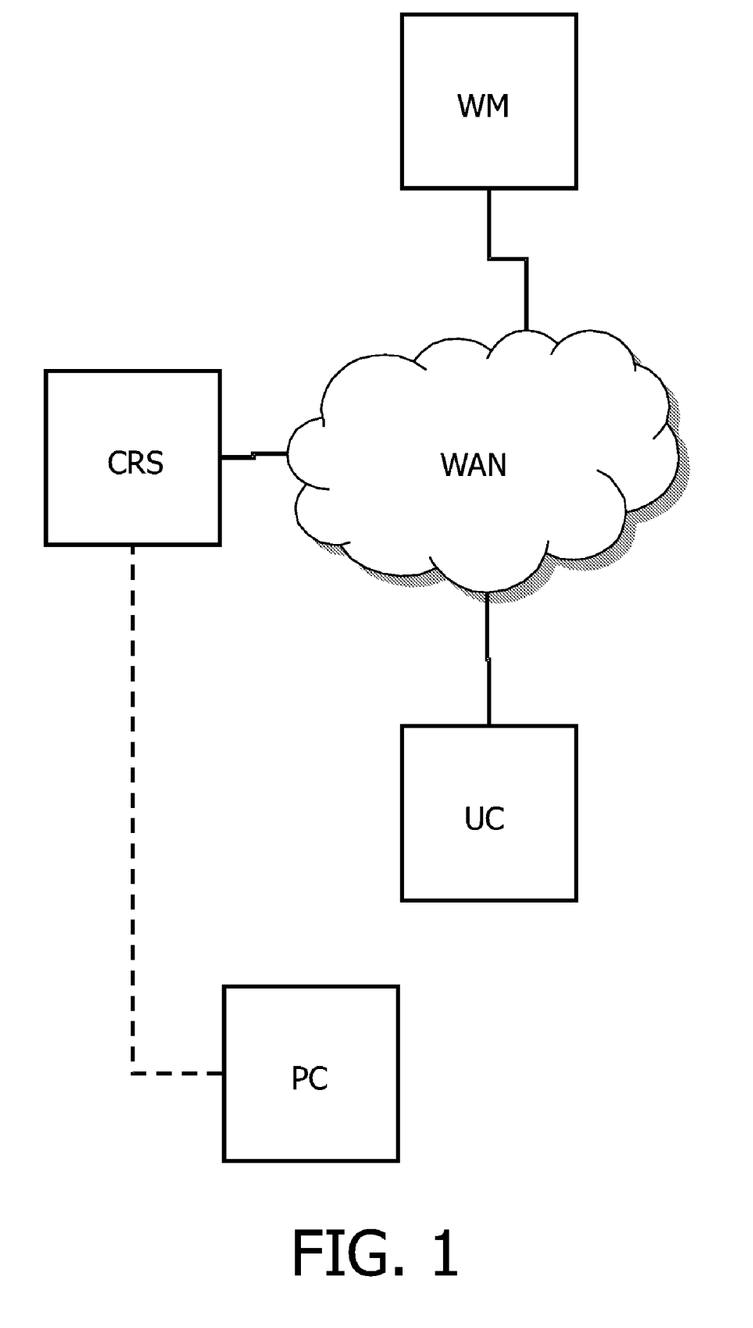
FIG. 1 schematically shows a basic embodiment of the weight management system according to the invention, FIG. 2 schematically shows a further embodiment of the weight management system according to the invention, FIG. 3 schematically shows an embodiment of the weight management module according to the invention, FIGS. 4 and 5 schematically show embodiments of the weight management system according to the invention, wherein the data input is automated, FIG. 6 schematically shows an embodiment of the weight management system according to the invention, comprising a calorie source group client, and FIG. 7 schematically shows an embodiment of the weight management system according to the invention, with an advanced user client.

FIG. 1 schematically shows a basic embodiment of the weight management system according to the invention. The weight management system comprises a weight management module WM for receiving information about a user's eating behavior via a cash register system CRS of a canteen, supermarket or restaurant or the like where the user buys food. The food intake information is sent to the weight management module WM together with a user ID that identifies the user. The user ID is provided by a personal card PC of the user. The food intake is used by the weight management module WM to calculate a calorie balance. The calorie balance is communicated to the user via a user client UC. The user client UC comprises output means, such as a display (not shown) for providing the calorie balance to the user. The calorie balance may, for example, comprise a survey of the calories consumed and/or a comparison of the consumed calories with a predetermined calorie budget. The weight management module WM may provide tips for future activities and choices of food. The coupling between the cash register system CRS, user client UC and weight management module WM is realized via a wide area network WAN, such as the Internet or a telephone network. For the purpose of communication, the weight management module WM, cash register system CRS and user client UC comprise sending and receiving means. The sending and receiving means may function wired or wireless and may use any type of sending/receiving technique, known in the art.

Figure 2:
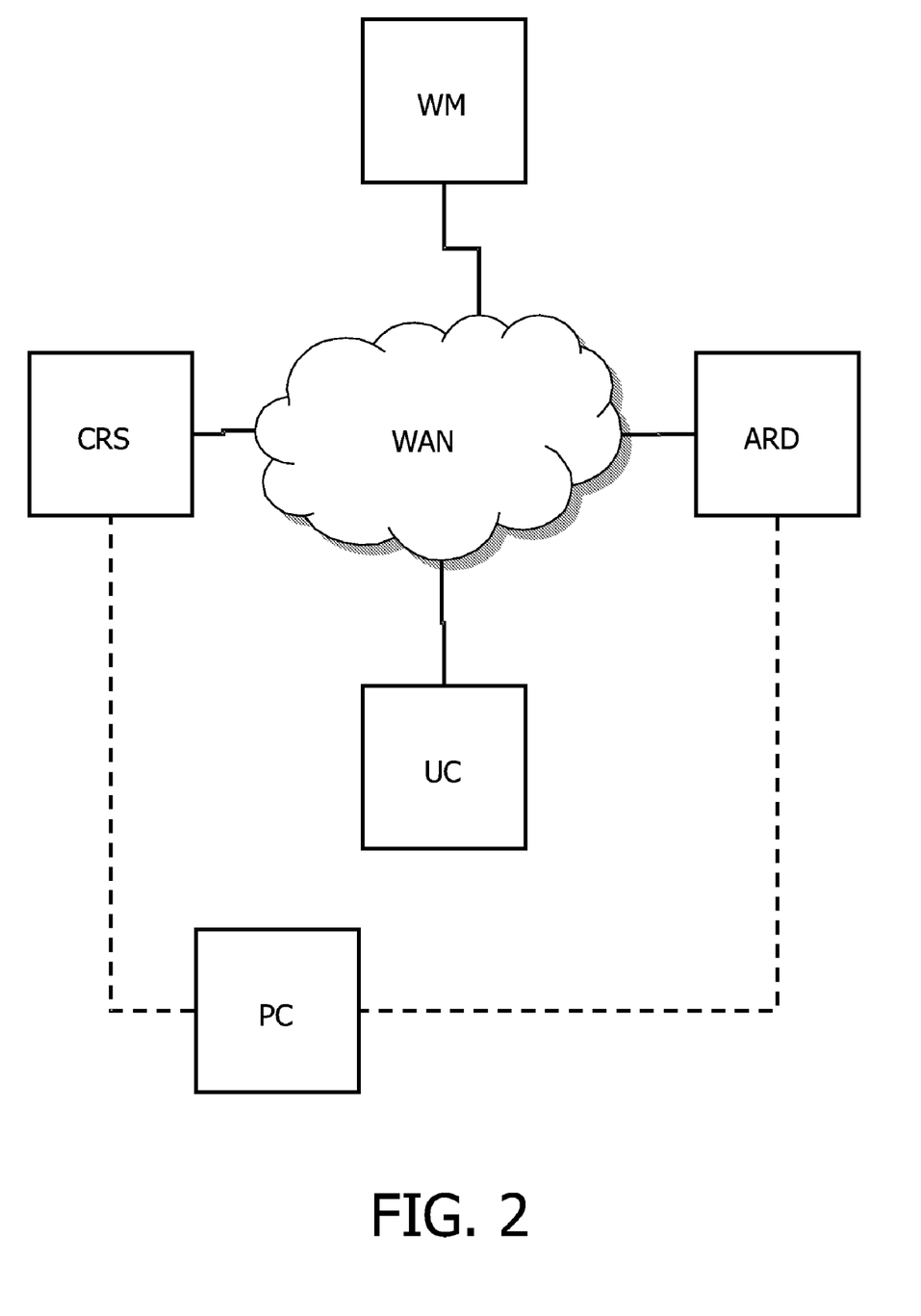

FIG. 2 schematically shows a further embodiment of the weight management system according to the invention. The weight management system further comprises an activity registration device ARD for registering activities performed by the user and sending information about the performed activities to the weight management module WM. The activity information is sent to the weight management module WM together with a user ID which identifies the user. The user ID is provided by a personal card PC of the user. The food intake and activity information are used by the weight management module WM to calculate the calorie balance. The calorie balance may comprise a survey of the calories consumed and expended and may provide tips for future activities and choices of food. The coupling between the activity registration device ARD and the weight management module WM is realized via the wide area network WAN. For the purpose of communication, the activity registration device ARD comprises sending and receiving means. The sending and receiving means may function wired or wireless and may use any type of sending/receiving technique, known in the art.

Preferably, the system works with a large variety of cash register systems CRS and activity register devices ARD at different food suppliers and sports clubs. The calorie intake component CIC may comprise a converter (not shown) for converting the food intake information to a uniform weight management system format. This makes it easy for the weight management module to calculate the calorie balance using information which is gathered in all different situations.

Figure 3:
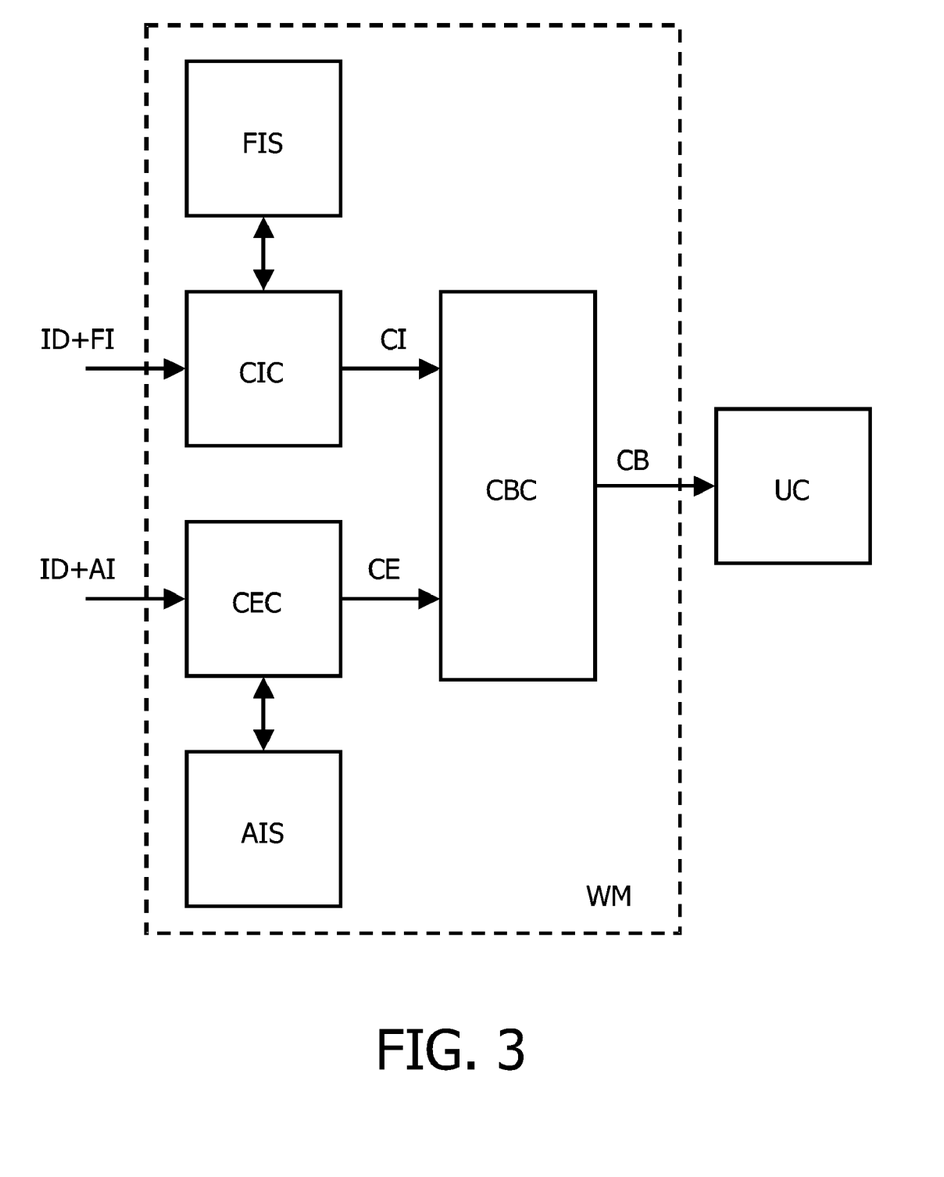

FIG. 3 schematically shows a basic embodiment of the weight management module WM according to the invention. The weight management module WM comprises a calorie intake component CIC and a calorie expenditure component CEC, which are both coupled to a calorie balance component CBC. The calorie intake component CIC receives information about the food a user consumes. Based on this information and on information about the consumed food from a food information server, the calorie content of the consumed food is calculated and sent to the calorie balance component CBC. In a similar way, the calorie expenditure component CEC calculates an amount of expended calories, based on information about a user's activities and an activity information server, and sends the amount to the calorie balance component CBC. Based on the consumed and expended calories, the calorie balance component CBC calculates whether the user has a calorie excess or a calorie deficit and provides the calculated results to the user client UC.

The user client UC may be realized in software for a personal computer, PDA or cell phone. The user client UC may also be realized as a dedicated weight management unit. The user client UC is coupled to the calorie balance component CBC via, for example, the Internet or a mobile network (e.g. GSM, GPRS, UMTS). The result of the calorie balance calculations may, for example, be provided as feedback about an observed eating and activity pattern, tips for future meals or activities or comparisons with eating and activity patterns of other, possibly imaginary, people. The user client UC may provide the opportunity to plan future behavior and, later, check whether the plan is correctly followed.

The calorie balance component CBC calculates all calorie intake and expenditure statistics for sending to the user client UC, based on the quantities of taken and expended calories as calculated by the calorie intake component CIC and the calorie expenditure component CEC respectively. The calorie balance component CBC is preferably realized as software for a central weight management server. In a preferred embodiment, not only a calorie balance is calculated, but also other important diet aspects, like the amounts of consumed fats, proteins, minerals and vitamins are monitored. For that purpose, a nutritional value monitor may be comprised in the weight management module WM.

The calorie intake component CIC and the calorie expenditure component CEC may be realized in the same weight management server as the calorie balance component CBC, but may also be realized on one or two separate computers which are coupled to the central weight management server. The calorie intake component CIC receives information about the type and amount of food a user consumes. For example, a food-based list may consist of either single-ingredient food items and weights or multiple-ingredient food items and total number of calories or other nutritional values (see Table 1).

TABLE 1

Examples of food lists with different food-based parameters

| F | Food Item | Nutrition Values | F | Food Item | gr/ml |
|---|---|---|---|---|---|
| F1 | Soup | 120 kcal | F1 | Cashew notes | 100 gr |
| F2 | Moussaka | 560 kcal | F2 | Fanta | 250 ml |
| F3 | Ice-cream cup | 320 kcal | F3 | Coffee | 150 ml |
| F4 | Cola | 170 kcal | F4 | . . . | |
| | Total | 1100 kcal | | | |

Preferably, all known food items have a code, which code is recognized by the food information system FIS. For the second food list in Table 1, the calorie intake component CIC looks up the nutritional values in a food information system FIS and calculates the amount of calories in the food items. In a similar way the calorie expenditure component CEC calculates the amount of calories expended by a user, using the activity information system AIS. Exemplary activity lists are shown in Table 2.

TABLE 2

Examples of activity lists with different activity-based parameters

| A | Activity Item | Expenditure | A | Activity Item | Duration |
|---|---|---|---|---|---|
| A1 | Jogging | 205 kcal | A1 | Cycling | 30 min |
| A2 | Steps | 360 kcal | A2 | Rowing | 30 min |
| | Total | 565 kcal | | | |

Figure 4:
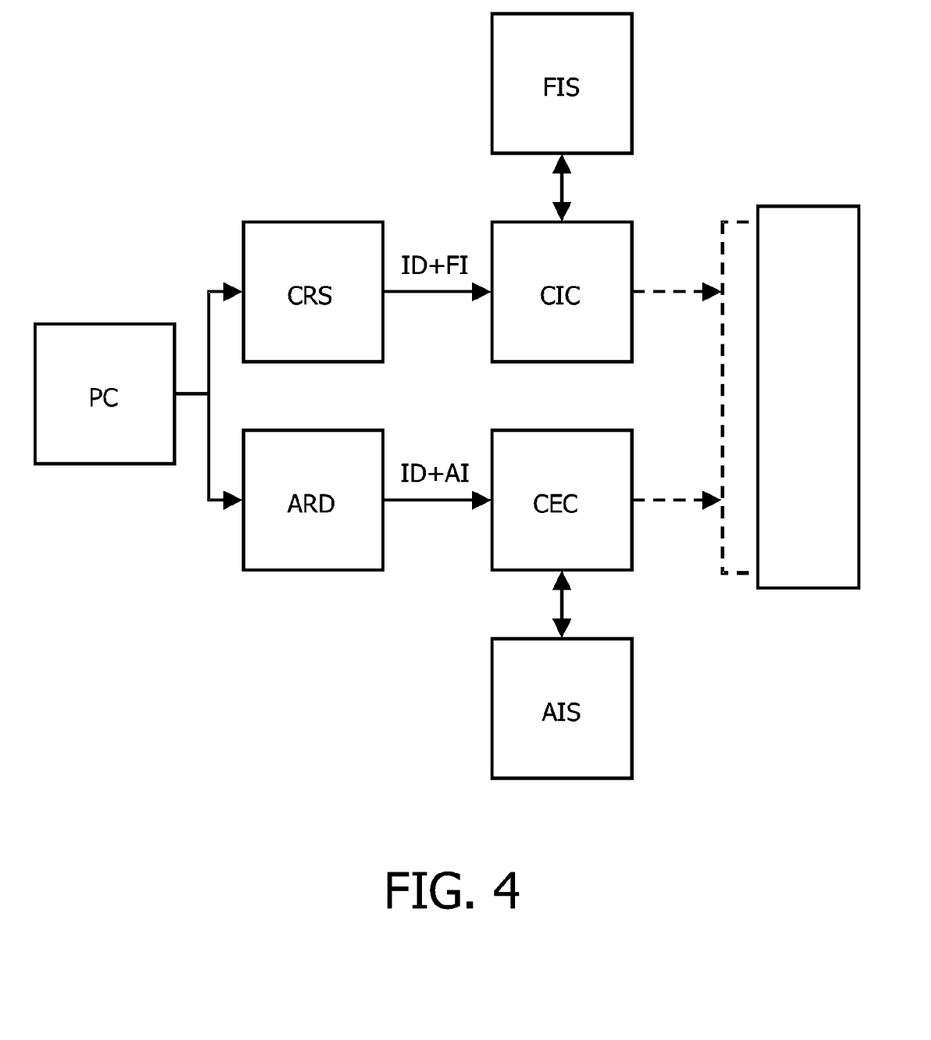
Figure 5:
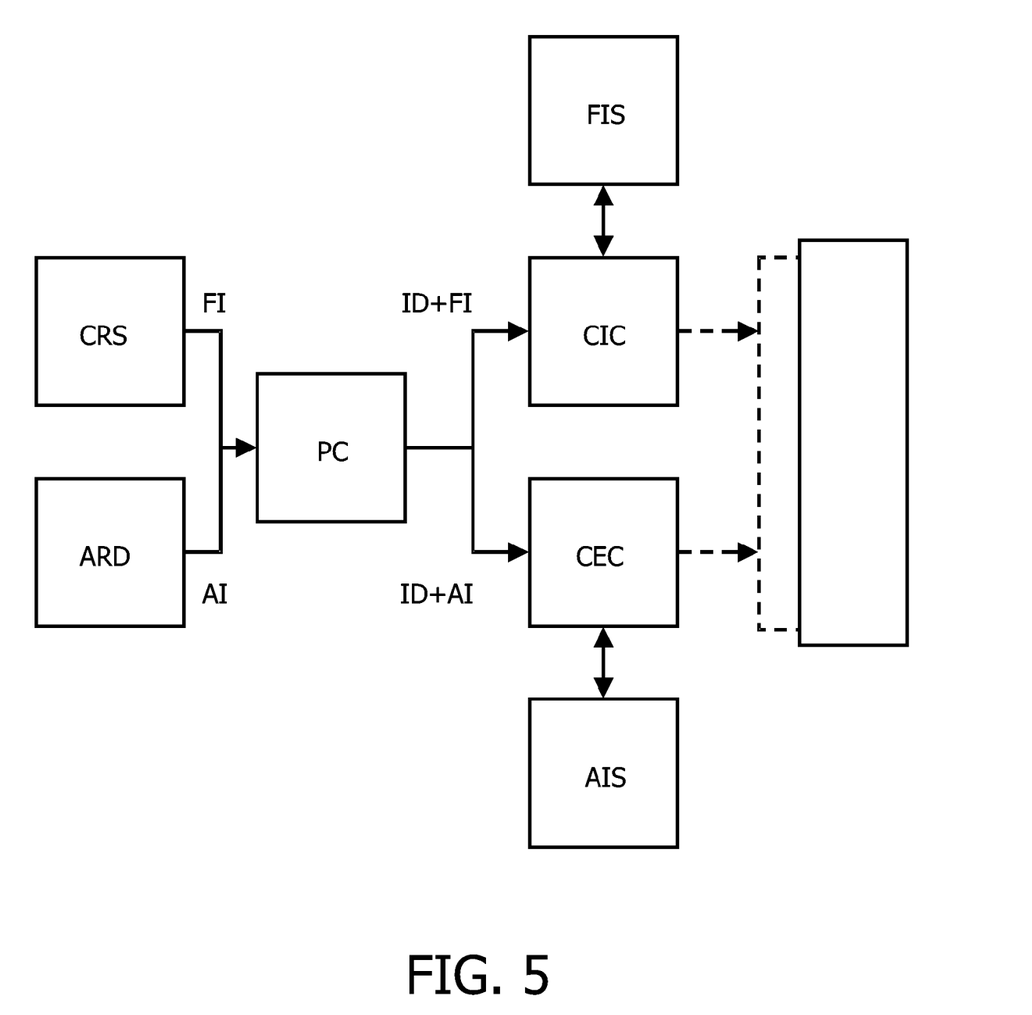

FIGS. 4 and 5 schematically show embodiments of the weight management system according to the invention, wherein the data input is automated. In these embodiments the user owns a personal card PC, preferably a smart card or the like with a memory for storing data. When the user buys food at, for example, a restaurant, canteen or supermarket, and pays using the personal card PC, a list of the purchased food items is sent to the calorie intake component CIC (FIG. 4) or stored on the memory of the personal card PC (FIG. 5). In the event that the list is stored on the memory of the personal card PC, then the cash register system CRS does not have to be connected to the calorie intake component CIC and the list is sent to the calorie intake component CIC later. Data stored on the personal card PC may, for example, be sent to the calorie intake component CIC using a computer with a card reader, the computer being connected to the Internet. For enabling the weight management system to calculate a calorie balance for a specific user, not only the food list, but also a Weight Management User ID is sent to the calorie intake component CIC. For this purpose the Weight Management User ID is to be stored on the personal card PC. Alternatively, the personal card PC is a credit card or bankcard of which the credit/bankcard number is sent to a server of the Credit Card Company or bank. The server then returns the user's Weight Management User ID to the cash register system CRS, if the user is a registered user. In this event, the user's credit card or bankcard does not require memory for storing weight management data. The user can join the weight management program by simply registering to the service. The credit or bank card number itself could also be used as Weight Management User ID, but that would require the cash register system CRS to also send credit or bank card numbers of people not participating in the weight management program to the weight management server. For privacy reasons, this would not be preferable. Also a loyalty card, such as an Airmiles Card, may be used instead of a credit card.

By using the cash register system CRS for automatically sending the list of purchased food items to the calorie intake component CIC when paying, the administration of consumed calories is fully automated. Existing weight management systems often use manual input of the consumed products which is time-consuming and especially in crowded public areas, like canteens, restaurants, and supermarkets, even inapplicable. Users often either do not have that opportunity or forget. Entry at a later moment is typically inaccurate due to the limited ability of users to exactly register what they ate.

In a similar way as wherein the cash register system CRS is used for automatically registering calorie intake, a member registration system is used for automatically registering activities. When a user goes to sports or fitness clubs, the associated member registration system checks (or gets informed) whether the user is subscribed to a weight management system. The information, e.g. Weight Management User ID and a weight management system identifier (e.g. URI/URL), can be stored on the user's personal card(s) PC, or can be looked up in a separate database. If the user is subscribed to a weight management system, the following steps are performed. A member registration system in a fitness club sends a list of activity-based parameters A1-Am to the weight management server. The weight management server can receive information from multiple member registration systems, e.g. a fitness club (training on Mondays and Wednesdays), and a dance club (dance lessons on Fridays).

The personal PC card may communicate with the cash register system CRS and/or activity registration device ARD via a card reader device. Preferably, the personal card communicates with the cash register system CRS contact less, for example, by using known techniques such as RFID. Alternatively, a mobile phone may be used instead of the personal card for providing a unique code, which is related to the Weight Management User ID.

Other devices for registering activities may include, a GPS unit for measuring a distance ran or walked by the user, a heart rate measurement device or a cycle computer. Such devices may be directly coupled to the weight management module WM or may temporarily store the activity data for future uploading.

Figure 6:
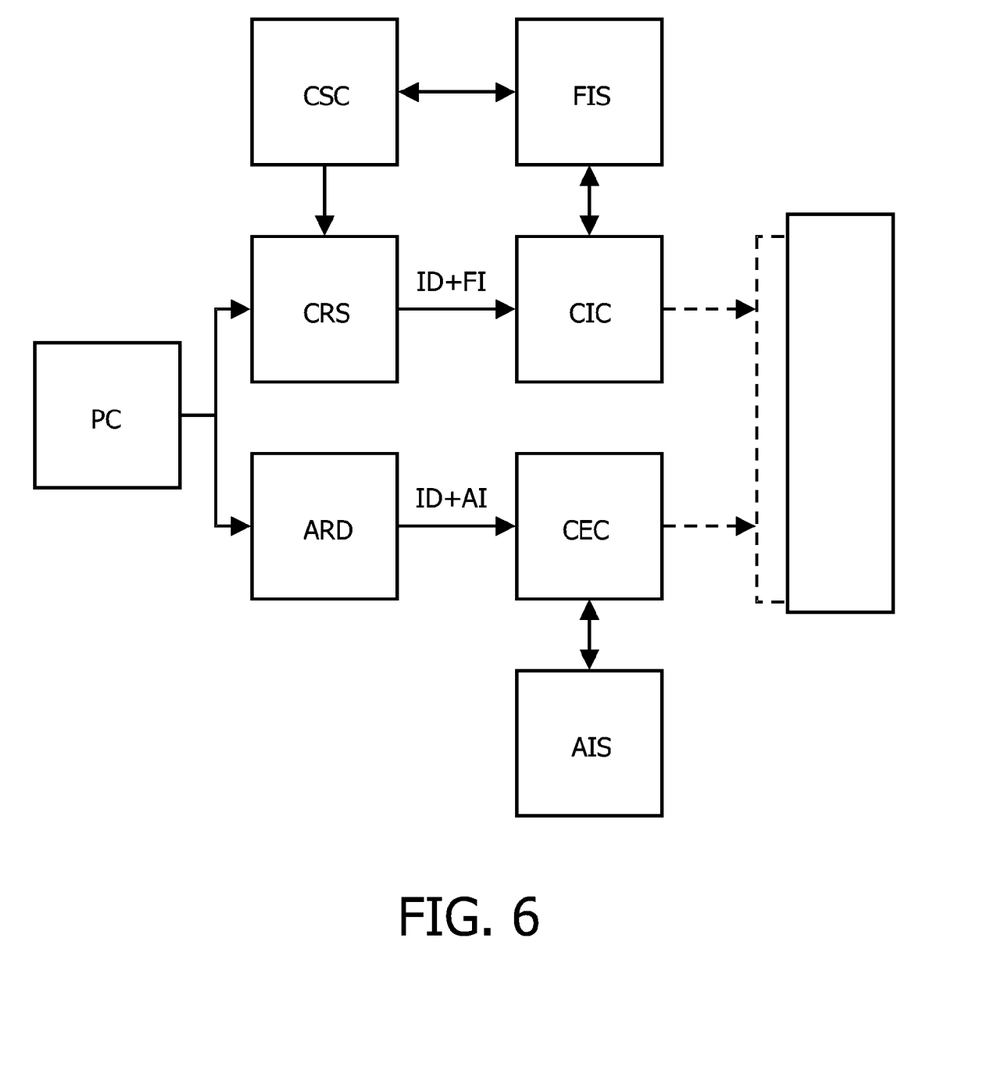

FIG. 6 schematically shows an embodiment of the weight management system according to the invention, comprising a calorie source group client. The calorie source client is coupled to the cash register system CRS of, for example, a restaurant and to the food information system FIS. When a restaurant offers a new food item or menu, the calorie source client connects with the food information system FIS and sends a list of the used ingredients to the food information server. The food information may then return the amount calories in the new food item or menu. The food information system FIS may also return a new code for identifying the new food item. The calorie source group client may then provide the new code, optionally with the calculated calorie value to the cash register system CRS. When someone buys the new food item, the new code is sent to the calorie intake component CIC and the purchasing of the food item will be taken into account for calculating the calorie balance.

Figure 7:
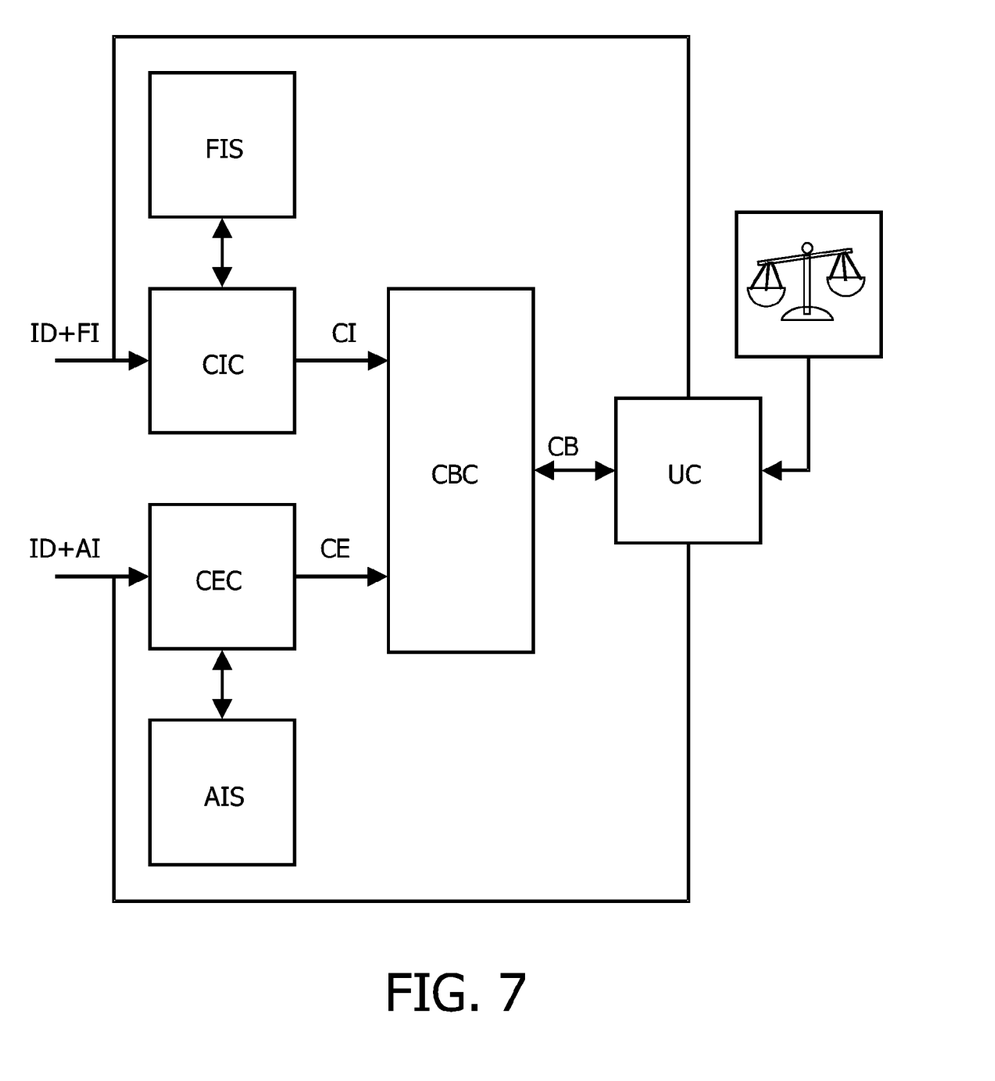

FIG. 7 schematically shows an embodiment of the weight management system according to the invention, with an advanced user client UC. The advanced user client UC may, for example, permit the user to input food items to the calorie intake component CIC manually using input means, such as a keyboard or mouse. This might be useful, for example, when eating something that is not bought in a shop which does not participate in the weight management system. The user may also be enabled to adjust a list of consumed food. For example, when a user only eats half of a bowl of soup he has bought, that should be taken into account when calculating the total amount of calories consumed in a particular period. Similarly, the user may, e.g., also add activities performed outside the fitness club to a list of performed activities. Furthermore the advanced user client UC may interact with the calorie balance component CBC, by planning future eating/activities, comparing a planning to actual behavior, or by requesting specific statistics. In a preferred embodiment the user client UC system is coupled to a weight scale. This scale enables the calorie balance component CBC to compare the actual user weight with his energy balance and to give user feedbacks. It also enables the calorie balance component CBC to generate recommendations depending on the body mass index (BMI) and the calorie balance.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to realize an advantage.

The invention claimed is:

1. A weight management system comprising:
 a personal card with a code, the code identifying a user to a cash register and being related to a user ID
 a cash register, a user client and a weight management module, coupled via a wide area network, the cash register being coupled to the weight management module via the wide area network for sending, when the user pays a food item, corresponding food intake information and the user ID to a weight management module, the user client being arranged for obtaining a calorie balance from the weight management module and comprising output means for providing the calorie balance to the user, and the weight management module comprising:
 a food information system for storing respective calorie content for a plurality of food items,
 a calorie intake component, coupled to the food information system, for calculating an amount of calories taken by the user based on the received food intake information, and
 a calorie balance component, coupled to the calorie intake component, for calculating a calorie balance for the user, based on the amount of calories taken by the user.

2. The weight management system according to claim 1, further comprising:
 a further personal card with a further code, the further code identifying a user to an activity registration device and being related to the user ID
 the activity registration device being coupled to the weight management module via the wide area network and being arranged for registering a performance of an activity sending the corresponding activity information and the user ID to the weight management module, the weight management module further comprising:
an activity information system for storing a respective calorie expense for a plurality of activities,
a calorie expenditure component, coupled to the activity information system, for calculating an amount of calories expended by the user based on the received activity information, and wherein
the calorie balance component is further coupled to the calorie expenditure component and is arranged for calculating the calorie balance further based on the amount of calories expended by the user.

3. The weight management system according to claim 2, wherein the user provides food intake information and activity information and sends the food intake information and the activity information to the weight management module.

4. The weight management system according to claim 2, wherein the activity information is formatted according to a uniform weight management system format.

5. The weight management system according to claim 2, wherein the calorie expenditure component comprises a converter which converts the activity information to a uniform weight management system format.

6. An activity registration device for use in the weight management system according to claim 2, comprising:
a registration device which, when the user performs an activity, registers the performance; and
a communication device which sends corresponding activity information and the user ID to the weight management module.

7. The weight management system according to claim 1, wherein the user client provides food intake information and sends the food intake information to the weight management module.

8. The weight management system according to claim 1, wherein the food intake information is formatted according to a uniform weight management system format.

9. The weight management system according to claim 1, wherein the calorie intake component comprises a converter which converts the food intake information to a uniform weight management system format.

10. The weight management system as claimed in claim 1, wherein the food information system comprises a calorie content for a plurality of food ingredients, the weight management system further comprising a calorie source group client, coupled to the food information system for calculating the food intake information for a new food item, based on a list of ingredients of the new food item.

11. The weight management system according to claim 1, wherein the code is the user ID.

12. The weight management system according to claim 1, wherein the code is one of a credit card number, a bank account number and a member registration number, and wherein the weight management system further comprises a database for relating the code to the user ID.

13. The weight management system according to claim 1, wherein the personal card is a smart card.

14. The weight management system according to claim 1, wherein
the food information system further stores at least one respective nutritional value other than the calorie content for the plurality of food items,
the calorie intake component further calculates a total amount of the at least one nutritional value taken by the user, and the weight management module further comprises a nutritional value monitor which monitors a nutritional value balance for the user, based on the amount of the at least one nutritional value taken by the user,
the user client obtains the nutritional value balance from the weight management module and the output means provides the nutritional value balance to the user.

15. A personal card for use in the weight management system according to claim 1, comprising the user ID and at least one of a credit card number, a bank account number and a member registration number.

16. A weight management system comprising:
a cash register system which reads user IDs from personal cards, food identifications which identify food items purchased, and credit card information and which includes an output for outputting the user IDs, food identifications, and credit card information to a wide area network;
a weight management module connected to the wide area network which receives the user IDs and food identifications from the cash register system, the weight management module including: a food information system which stores at least calorie content of the food items identified by the food identifications, a calorie intake component which calculates an amount of calories taken by the user based on the calorie contents from the food information system of the food items output by the cash register system with the ID of a selected user, and a calorie balance component which compares the calculated amount of calories taken with a calorie budget and calculates a calorie balance based on the comparison; and
a plurality of wireless user client devices each associated with a corresponding user ID and connected with the wide area network, each user client device including a display on which an output of the calorie balance component is displayed.

17. The weight management system as claimed in claim 16, wherein the food items include restaurant menu food items and calories for each menu food item are stored in a restaurant data base which is connected with the wide area network and wherein the food information system accesses the restaurant database to retrieve calorie contents for the restaurant menu food items.

18. The weight management system as claimed in claim 16, further including at least one piece of exercise equipment connected with a personal card reader which reads user IDs from the personal cards and communicates the personal IDs and exercise activity information via the wide area network to the weight management module, the weight management module further including:
an activity information system which stores calorie expense amounts for each of a plurality of exercise activities;
a calorie expenditure component which calculates an amount of calories expended by the user associated with a corresponding user ID based on the received activity information and the calorie expense information from the activity information system; and
the calorie balance component generating the calorie balance based on the comparison and the amount of calories expended by the identified user.

19. A weight management system comprising:
a cash register system which reads user IDs from personal cards and food identifications which identify food items purchased by users identified by one of the user IDs carried on one of the personal cards presented at a time of purchase, the cash register system being connected with a wide area network for outputting identifications of food items and corresponding user IDs; and at least one processor connected with the wide area network and programmed to perform the steps of:

storing respective calorie content amounts for each of a plurality of food items identified by the food identifications;

calculating an amount of calories taken in by a corresponding user in each purchase from the cash register system based on the calorie content of the food items identified by the cash register system and the corresponding user ID output by the cash register system;

calculating a calorie balance for the corresponding user based on the calorie content amount, any prior calorie balance for the corresponding user, and a calorie budget for the corresponding user calculated by the calorie balance component, each user client device including a display on which the calorie balance calculated by the calorie balance component for the corresponding user ID is calculated;

transmitting the calorie balance via the wide area network for the corresponding user ID; and a plurality of wireless user client devices each associated with a corresponding user ID and connected with the wide area network to receive the calorie balance associated with the corresponding user ID, each user client device including a display on which the calculated calorie balance corresponding to the user ID of the user client device is displayed.

* * * * *